(12) United States Patent  
Hunziker et al.

(10) Patent No.: US 8,703,807 B2  
(45) Date of Patent: *Apr. 22, 2014

(54) AZASPIRODECANONE COMPOUNDS

(75) Inventors: Daniel Hunziker, Moehlin (CH); Werner Neidhart, Hagenthal-le-Bas (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/414,749

(22) Filed: Mar. 8, 2012

(65) Prior Publication Data

US 2012/0238594 A1    Sep. 20, 2012

(30) Foreign Application Priority Data

Mar. 17, 2011   (EP) .................................. 11158703

(51) Int. Cl.  
*A61K 31/4015*   (2006.01)  
*C07D 209/54*   (2006.01)

(52) U.S. Cl.  
USPC ........... 514/409; 548/407; 548/408; 546/184; 546/208; 514/317; 514/326

(58) Field of Classification Search  
USPC ........... 548/407, 408; 546/184, 208; 514/315, 514/317, 326, 409  
See application file for complete search history.

(56) References Cited

U.S. PATENT DOCUMENTS

| 7,968,585 | B2 * | 6/2011 | Mabry et al. .................. 514/409 |
| 8,097,634 | B2 * | 1/2012 | Ackermann et al. .......... 514/278 |
| 8,329,904 | B2 * | 12/2012 | Ackermann et al. ............ 546/16 |
| 2010/0292212 | A1 | 11/2010 | Ackermann et al. |

FOREIGN PATENT DOCUMENTS

WO    2011/045292    4/2011

OTHER PUBLICATIONS

Ackermann et al (2011): STN International HCAPLUS database, (Columbus, Ohio), Accession No. 2011:497600.*  
Buchwald et al., "Journal of the American Chemical Society" 124:7421 ( 2002).  
"International Search Report PCT/EP2012/054410 mailed Apr. 24, 2012".

* cited by examiner

*Primary Examiner* — Golam M M Shameem

(57) ABSTRACT

The invention provides novel compounds having the general formula (I)

(I)

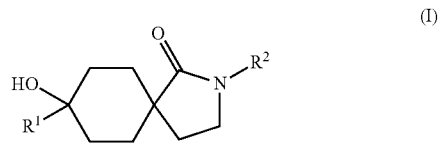

wherein $R^1$ and $R^2$ are as described herein, compositions including the compounds, their pharmaceutically acceptable salts and esters and methods of using the compounds.

39 Claims, No Drawings

AZASPIRODECANONE COMPOUNDS

PRIORITY TO RELATED APPLICATIONS

This application claims the benefit of European Patent Application No. 11158703.6, filed Mar. 17, 2011, which is hereby incorporated by reference in its entirety.

FIELD OF THE INVENTION

The present invention relates to organic compounds useful for therapy or prophylaxis in a mammal, and in particular to inhibitors of hormone sensitive lipase (HSL) for the treatment of diabetes, metabolic syndrome, dyslipidemia, atherosclerosis, obesity, cardiovascular diseases, myocardial dysfunction, inflammation, nonalkoholic fatty liver disease or nonalkoholic steatohepatitis.

BACKGROUND OF THE INVENTION

The main physiological role of white adipose tissue (WAT) is to supply energy when it is needed by other tissues. In mammals, white adipose tissue is the primary energy storage depot, accumulating fuel reserves in the form of triacylglycerol (TAG) during times of energy excess. The release of free fatty acids (FFA) from TAG is stimulated by catecholamines and regulated by hormones such as insulin, glucagon and epinephrine. The most important enzyme in WAT believed responsible for hormone regulated hydrolysis of triglyceride is hormone sensitive lipase (HSL).

Dysregulation of adipocyte lipolysis, resulting in elevated circulating non-esterified fatty acids (NEFA) is associated with obesity and co-morbidities including the development of type 2 diabetes. Obese or insulin resistant subjects have increased visceral adipose tissue depots. These depots contain elevated levels of HSL protein and exhibit enhanced lipolytic activity as they are resistant to the insulin-mediated suppression of lipolysis. This results in increased plasma levels of free fatty acids (FFA), which further exacerbates insulin resistance due to the accumulation of triglycerides in tissues other than WAT such as liver, pancreas and muscle. Thus, the elevated plasma levels of FFA due to increased HSL activity contributes to and worsens insulin resistance in obese and type 2 diabetic individuals. Restoring the exaggerated plasma FFA and triglyceride levels through inhibition of HSL would reduce the accumulation of triglycerides in tissues other than WAT, such as liver, muscle and the pancreas resulting in decreased hepatic glucose output, increased muscle fatty acid oxidation and improving β-cell function.

Elevated FFAs are also associated with increased cardiovascular risk, including atherosclerosis and myocardial dysfunction. Furthermore high lipolytic activity and elevated FFAs lead to increased insulin resistance and hypertension in hypertensive rats. The FFA collect in the liver and lead to increased production of TAG, which are packaged into very low density lipoproteins (VLDL) which are secreted. Therefore, reducing the activity of HSL would decrease the release of FFA to the blood, thus limiting the supply of FFA to the liver for TAG synthesis. Thus, HSL inhibitors could have beneficial effects as treatment of nonalkoholic fatty liver disease (NAFLD) and nonalkoholic steatohepatitis (NASH).

Objects of the present invention are the compounds of formula (I) and their aforementioned salts and esters and their use as therapeutically active substances, a process for the manufacture of the said compounds, intermediates, pharmaceutical compositions, medicaments containing the said compounds, their pharmaceutically acceptable salts or esters, the use of the said compounds, salts or esters for the treatment or prophylaxis of illnesses, especially in the treatment or prophylaxis of diabetes, metabolic syndrome, dyslipidemia, atherosclerosis, obesity, cardiovascular diseases, myocardial dysfunction, inflammation, nonalkoholic fatty liver disease or nonalkoholic steatohepatitis and the use of the said compounds, salts or esters for the production of medicaments for the treatment or prophylaxis of diabetes, metabolic syndrome, dyslipidemia, atherosclerosis, obesity, cardiovascular diseases, myocardial dysfunction, inflammation, nonalkoholic fatty liver disease or nonalkoholic steatohepatitis.

SUMMARY OF THE INVENTION

The present invention relates to a compound of formula (I)

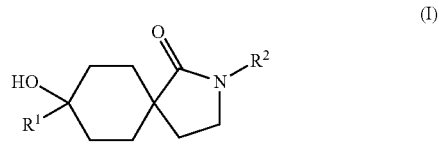

(I)

wherein
$R^1$ is selected from the group consisting of haloalkoxyalkyl, oxopyrrolydinylalkyl and oxopiperidinylalkyl; and
$R^2$ is substituted phenyl or substituted pyridinyl, wherein substituted phenyl and substituted pyridinyl are substituted with one to three substituents independently selected from the group consisting of haloalkyl, hydroxyhaloalkyl, alkoxy and haloalkoxy;
or a pharmaceutically acceptable salt or ester thereof.

The present invention also relates to a pharmaceutical composition comprising a compound as described above and a therapeutically inert carrier.

DETAILED DESCRIPTION OF THE INVENTION

The term "alkoxy" denotes a group of the formula —O—R', wherein R' is an alkyl group. Examples of alkoxy group include methoxy, ethoxy, n-propoxy, isopropoxy, n-butoxy, isobutoxy and tert-butoxy. Particular alkoxy group include methoxy, ethoxy, n-propoxy and isopropoxy. Further particular example is isopropoxy.

The term "alkyl" denotes a monovalent linear or branched saturated hydrocarbon group of 1 to 12 carbon atoms, in particular of 1 to 7 carbon atoms, more particular of 1 to 4 carbon atoms, for example, methyl, ethyl, n-propyl, isopropyl, n-butyl, iso-butyl, sec-butyl, and tert-butyl. Particular alkyl groups include methyl, ethyl, n-propyl and isopropyl. More particular alkyl group is methyl.

The term "haloalkoxy" denotes an alkoxy group wherein at least one of the hydrogen atoms of the alkoxy group has been replaced by same or different halogen atoms. Examples of haloalkoxy include fluoromethoxy, difluoromethoxy, trifluoromethoxy, trifluoroethoxy, trifluoromethylethoxy, trifluorodimethylethoxy and pentafluoroethoxy. Particular haloalkoxy groups are trifluoromethoxy and trifluoroethoxy. More particular haloalkoxy group is 1,1,1-trifluoropropan-2-oxy.

The term "haloalkyl" denotes an alkyl group wherein at least one of the hydrogen atoms of the alkyl group has been replaced by same or different halogen atoms. Examples of haloalkyl include fluoromethyl, difluoromethyl, trifluoromethyl, trifluoroethyl, trifluoromethylethyl and pentafluoroethyl. Particular haloalkyl group is trifluoromethyl.

The term "halogen" and "halo" are used interchangeably herein and denote fluoro, chloro, bromo, or iodo. Particular halogens are chloro and fluoro. More particular halogen is fluoro.

The term "hydroxyhaloalkyl" denotes an alkyl wherein at least one of the hydrogen atoms of the alkyl has been replaced by a hydroxy group and wherein at least one of the hydrogen atoms of the alkyl has been replaced by a halogen. Examples of hydroxyhaloalkyl include hydroxytrifluoroethyl, hydroxytrifluoropropyl and hydroxyhexafluoropropyl. Particular hydroxyhaloalkyl is 2,2,2-trifluoro-1-hydroxyethyl.

The term "oxo" denotes a divalent oxygen atom =O.

The term "oxopiperidinyl" denotes a piperidinyl wherein two geminal hydrogens atoms of the piperidinyl have been replaced by an oxo group. Particular example is 2-oxopiperidinyl.

The term "oxopyrrolydinyl" denotes a pyrrolydinyl wherein two geminal hydrogens atoms of the pyrrolydinyl have been replaced by an oxo group. Particular example is 2-oxopyrrolydinyl.

The term "oxopiperidinylalkyl" denotes an alkyl wherein at least one of the hydrogen atoms of the alkyl has been replaced by an oxopiperidinylalkyl group. Particular example is 2-oxopiperidin-1-ylmethyl.

The term "oxopyrrolydinylalkyl" denotes an alkyl wherein at least one of the hydrogen atoms of the alkyl has been replaced by an oxopyrrolydinyl group. Particular example is 2-oxopyrrolydin-1-ylmethyl.

The present invention relates to a compound of formula (I)

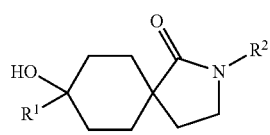

(I)

wherein
$R^1$ is selected from the group consisting of haloalkoxyalkyl, oxopyrrolydinylalkyl and oxopiperidinylalkyl; and
$R^2$ is substituted phenyl or substituted pyridinyl, wherein substituted phenyl and substituted pyridinyl are substituted with one to three substituents independently selected from the group consisting of haloalkyl, hydroxyhaloalkyl, alkoxy and haloalkoxy;
or a pharmaceutically acceptable salt or ester thereof.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are the hydrochloride salts, methanesulfonic acid salts and citric acid salts.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The term "protecting group" (PG) denotes the group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. Particular protecting groups are the tert-butoxycarbonyl (Boc), benzyloxycarbonyl (Cbz), fluorenylmethoxycarbonyl (Fmoc) and benzyl (Bn). Further particular protecting groups are the tert-butoxycarbonyl (Boc) and the fluorenylmethoxycarbonyl (Fmoc). More particular protecting group is the benzyl group (Bn).

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

Also an embodiment of the present invention are compounds according to formula (I) as described herein and pharmaceutically acceptable salts or esters thereof, in particular compounds according to formula (I) as described herein and pharmaceutically acceptable salts thereof, more particularly compounds according to formula (I) as described herein.

A further embodiment of the present invention are compounds according to formula (I) as described herein, wherein $R^1$ is haloalkoxyalkyl or oxopyrrolydinylalkyl.

A particular embodiment of the present invention are compounds according to formula (I) as described herein, wherein $R^1$ is haloalkoxyalkyl.

In a further embodiment of the present invention are compounds according to formula (I) as described herein, wherein $R^1$ is selected from the group consisting of 2-fluoroethoxymethyl, 2,2-difluoroethoxymethyl and 2,2,2-trifluoroethoxymethyl.

Another further embodiment of the present invention are compounds according to formula (I) as described herein, wherein $R^1$ is 2-fluoroethoxymethyl or 2,2-difluoroethoxymethyl.

Another embodiment of the present invention are compounds according to formula (I) as described herein, wherein $R^1$ is 2-fluoroethoxymethyl.

The present invention also relates to compounds according to formula (I) as described herein, wherein $R^1$ is 2,2-difluoroethoxymethyl.

A further particular embodiment of the present invention are compounds according to formula (I) as described herein, wherein $R^1$ is 2,2,2-trifluoroethoxymethyl.

A more particular embodiment of the present invention are compounds according to formula (I) as described herein, wherein $R^1$ is oxopyrrolydinylalkyl.

Also an embodiment of the present invention are compounds according to formula (I) as described herein, wherein $R^1$ is 2-oxopyrrolydin-1-ylmethyl.

The present invention also relates to compounds according to formula (I) as described herein, wherein $R^1$ is oxopiperidinylalkyl.

Another embodiment of the present invention are compounds according to formula (I) as described herein, wherein $R^1$ is 2-oxopiperidin-1-ylmethyl.

A further particular embodiment of the present invention are compounds according to formula (I) as described herein, wherein $R^1$ is selected from the group consisting of 2-fluoroethoxymethyl, 2,2-difluoroethoxymethyl, 2,2,2-trifluoroethoxymethyl, 2-oxopyrrolydin-1-ylmethyl and 2-oxopiperidin-1-ylmethyl.

A particular embodiment of the present invention are compounds according to formula (I) as described herein, wherein $R^1$ is selected from the group consisting of 2-fluoroethoxymethyl, 2,2-difluoroethoxymethyl and 2-oxopyrrolydin-1-ylmethyl.

Also an embodiment of the present invention are compounds according to formula (I) as described herein, wherein $R^2$ is substituted phenyl or substituted pyridinyl, wherein substituted phenyl and substituted pyridinyl are substituted with one to three substituents independently selected from the group consisting of alkoxy and haloalkoxy.

The present invention also relates to compounds according to formula (I) as described herein, wherein $R^2$ is substituted phenyl or substituted pyridinyl, wherein substituted phenyl and substituted pyridinyl are substituted with one substituent selected from the group consisting of trifluoromethyl, 2,2,2-trifluoro-1-hydroxyethyl, isopropoxy and 1,1,1-trifluoropropan-2-yloxy.

Also an embodiment of the present invention are compounds according to formula (I) as described herein, wherein $R^2$ is substituted phenyl, wherein substituted phenyl is substituted with one to three substituents independently selected from the group consisting of haloalkyl, hydroxyhaloalkyl, alkoxy and haloalkoxy.

Another embodiment of the present invention are compounds according to formula (I) as described herein, wherein $R^2$ is substituted phenyl, wherein substituted phenyl is substituted with one substituent selected from the group consisting of haloalkyl, hydroxyhaloalkyl, alkoxy and haloalkoxy.

The present invention also relates to compounds according to formula (I) as described herein, wherein $R^2$ is substituted phenyl, wherein substituted phenyl is substituted with one substituent selected from the group consisting of trifluoromethyl, 2,2,2-trifluoro-1-hydroxyethyl, isopropoxy and 1,1,1-trifluoropropan-2-yloxy.

Also an embodiment of the present invention are compounds according to formula (I) as described herein, wherein $R^2$ is substituted phenyl, wherein substituted phenyl is substituted with one substituent selected from the group consisting of isopropoxy and 1,1,1-trifluoropropan-2-yloxy.

Also an embodiment of the present invention are compounds according to formula (I) as described herein, wherein $R^2$ is 4-(isopropoxy)phenyl or 4-(1,1,1-trifluoropropan-2-yloxy)phenyl.

Another embodiment of the present invention are compounds according to formula (I) as described herein, wherein $R^2$ is substituted phenyl, wherein substituted phenyl is substituted with one haloalkyl.

A particular embodiment of the present invention are compounds according to formula (I) as described herein, wherein $R^2$ is 4-(trifluoromethyl)phenyl.

A further particular embodiment of the present invention are compounds according to formula (I) as described herein, wherein $R^2$ is substituted phenyl, wherein substituted phenyl is substituted with one hydroxyhaloalkyl.

Also an embodiment of the present invention are compounds according to formula (I) as described herein, wherein $R^2$ is 4-(2,2,2-trifluoro-1-hydroxyethyl)phenyl.

Another embodiment of the present invention are compounds according to formula (I) as described herein, wherein $R^2$ is substituted phenyl, wherein substituted phenyl is substituted with one alkoxy.

A particular embodiment of the present invention are compounds according to formula (I) as described herein, wherein $R^2$ is 4-(isopropoxy)phenyl.

A further particular embodiment of the present invention are compounds according to formula (I) as described herein, wherein $R^2$ is substituted phenyl, wherein substituted phenyl is substituted with one haloalkoxy.

The present invention also relates to compounds according to formula (I) as described herein, wherein $R^2$ is 4-(1,1,1-trifluoropropan-2-yloxy)phenyl.

Another embodiment of the present invention are compounds according to formula (I) as described herein, wherein $R^2$ is substituted pyridinyl, wherein substituted pyridinyl is substituted with one to three substituents independently selected from the group consisting of haloalkyl, hydroxyhaloalkyl, alkoxy and haloalkoxy.

A further particular embodiment of the present invention are compounds according to formula (I) as described herein, wherein $R^2$ is substituted pyridinyl, wherein substituted pyridinyl is substituted with one substituent selected from alkoxy and haloalkoxy.

The present invention also relates to compounds according to formula (I) as described herein, wherein $R^2$ is substituted pyridinyl, wherein substituted pyridinyl is substituted with one substituent selected from isopropoxy and 1,1,1-trifluoropropan-2-yloxy.

A particular embodiment of the present invention are compounds according to formula (I) as described herein, wherein $R^2$ is 6-isopropoxypyridin-3-yl.

Another embodiment of the present invention are compounds according to formula (I) as described herein, wherein $R^2$ is 6-(1,1,1-trifluoropropan-2-yloxy)pyridin-3-yl.

A further embodiment of the present invention are compounds according to formula (I) as described herein of formula (Ia)

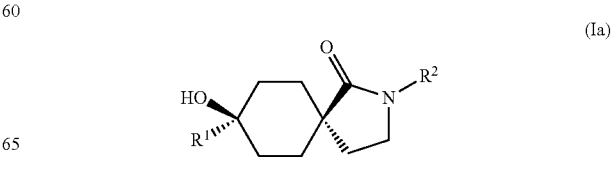

(Ia)

Also a further embodiment of the present invention are compounds according to formula (I) as described herein of formula (Ib)

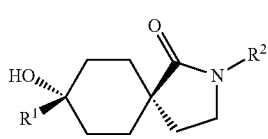

Particular examples of compounds of formula (I) as described herein are selected from the group consisting of:
(5α,8α)-8-hydroxy-8-((2-oxopyrrolidin-1-yl)methyl)-2-(4-(trifluoromethyl)phenyl)-2-azaspiro[4.5]decan-1-one
(5α,8α)-8-Hydroxy-8-(2-oxo-piperidin-1-ylmethyl)-2-(4-trifluoromethyl-phenyl)-2-aza-spiro[4.5]decan-1-one
(5α,8α)-8-hydroxy-2-(4-isopropoxyphenyl)-8-((2-oxopyrrolidin-1-yl)methyl)-2-azaspiro[4.5]decan-1-one
(5α,8α)-8-hydroxy-2-(4-isopropoxyphenyl)-8-((2-oxopiperidin-1-yl)methyl)-2-azaspiro[4.5]decan-1-one
(5α,8α)-8-(2,2-Difluoro-ethoxymethyl)-8-hydroxy-2-(4-isopropoxy-phenyl)-2-aza-spiro[4.5]decan-1-one
(5α,8α)-8-Hydroxy-2-(6-isopropoxy-pyridin-3-yl)-8-(2-oxo-pyrrolidin-1-ylmethyl)-2-aza-spiro[4.5]decan-1-one
(5α,8α)-8-hydroxy-2-(6-isopropoxypyridin-3-yl)-8-(2,2,2-trifluoroethoxy)methyl)-2-azaspiro[4.5]decan-1-one
(5α,8α)-8-Hydroxy-8-(2-oxo-pyrrolidin-1-ylmethyl)-2-[4-((R)-2,2,2-trifluoro-1-hydroxy-ethyl)-phenyl]-2-aza-spiro[4.5]decan-1-one
(5α,8α)-8-hydroxy-8-((2-oxopyrrolidin-1-yl)methyl)-2-(4-((R)-1,1,1-trifluoropropan-2-yloxy)phenyl)-2-azaspiro[4.5]decan-1-one
(5α,8α)-8-hydroxy-8-((2-oxopyrrolidin-1-yl)methyl)-2-(6-((S)-1,1,1-trifluoropropan-2-yloxy)pyridin-3-yl)-2-azaspiro[4.5]decan-1-one
(5α,8α)-8-(2-fluoroethoxy)methyl)-8-hydroxy-2-(6-((S)-1,1,1-trifluoropropan-2-yloxy)pyridin-3-yl)-2-azaspiro[4.5]decan-1-one
(5α,8α)-8-(2-fluoroethoxy)methyl)-8-hydroxy-2-(4-isopropoxyphenyl)-2-azaspiro[4.5]decan-1-one; and pharmaceutically acceptable salts thereof.

Further particular examples of compounds of formula (I) as described herein are selected from the group consisting of:
(5α,8α)-8-hydroxy-2-(4-isopropoxyphenyl)-8-((2-oxopyrrolidin-1-yl)methyl)-2-azaspiro[4.5]decan-1-one;
(5α,8α)-8-(2,2-Difluoro-ethoxymethyl)-8-hydroxy-2-(4-isopropoxy-phenyl)-2-aza-spiro[4.5]decan-1-one;
(5α,8α)-8-(2-fluoroethoxy)methyl)-8-hydroxy-2-(6-((S)-1,1,1-trifluoropropan-2-yloxy)pyridin-3-yl)-2-azaspiro[4.5]decan-1-one;
and pharmaceutically acceptable salts thereof.

Processes for the manufacture of compounds of formula (I) as described herein are an object of the invention.

The preparation of compounds of formula (I) of the present invention may be carried out in sequential or convergent synthetic routes. Syntheses of the invention are shown in the following general schemes. The skills required for carrying out the reaction and purification of the resulting products are known to those persons skilled in the art. In case a mixture of enantiomers or diastereoisomers is produced during a reaction, these enantiomers or diastereoisomers can be separated by methods described herein or known to the man skilled in the art such as e.g. chiral chromatography or crystallization. The substituents and indices used in the following description of the processes have the significance given herein. A relative configuration [5α,8α] on the 8-hydroxy-2-aza-spiro[4.5]decan-1-one backbone corresponds to cis configuration on the cyclohexane ring, whereas a relative configuration [5α,8β] corresponds to a trans configuration on the cyclohexane ring of compounds according to formula (I) as described above.

Compounds of formula (I) are readily accessible as outlined in scheme 1 by treating compounds of formula A8 with compounds of formula R¹—H as defined above in the presence of a base such as sodium hydride or potassium tert-butoxide in a solvent such as DMF, THF or tert-butanol or the like at a temperature comprised between RT and reflux.

Scheme 1

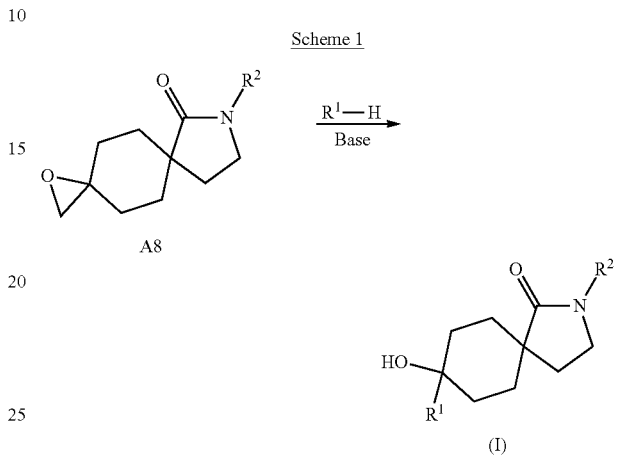

The compounds of formula R¹—H are either commercially available or described in the literature. The synthesis of intermediates of formula A8 are outlined in Schemes 2 and 3.

Thus, as outlined in scheme 2, commercially available ketone A1 can be protected for example as a ketal (step (a)) to give the compound A2 according to methods known in the literature. Ketal A2 is then alkylated at the appropriate position by treatment with a suitable base such as lithium diisopropylamide, lithium or sodium hexamethyldisilazane, potassium tert-butoxide or the like in an appropriate solvent such as THF, DMF, diethylether or the like followed by addition of the appropriate electrophile such as 1-bromo-2-methoxyethane to give compound A3 (step (b)). A3 can be isolated if desired or the ketal group can be removed (step (c)) during the workup of reaction step (b). Thus, treatment of crude A3 with a strong aqueous mineral acid such as HCl, $H_2SO_4$, HBr or the like at various temperatures ranging from −15° C. to 100° C. until hydrolysis of the ketal protecting group is completed (step (c)) gives compound A4.

Reduction of compound A4 (step (d)) can be accomplished with reducing agents such as $NaBH_4$ or similar in an appropriate solvent such as MeOH, EtOH or 2-propanol at 0° C. or elevated temperatures giving rise to compound A5 as mixtures of cis and trans isomers.

Subsequent transformation to compounds of formula A6 (as a mixture of cis/trans isomers) can be achieved according to Scheme 2 (step (e)) by treatment of A5 (as a mixture of cis/trans isomers) with appropriate compounds of formula R²—$NH_2$ and an appropriate organometallic reagent such as $(CH_3)_2AlCl$ or $Al(CH_3)_3$, in an appropriate solvent such as toluene, benzene, chloroform, dioxane or the like at a suitable temperature ranging from 0 to 150° C. to provide compounds of formula A6.

Subsequent oxidation of compounds of formula A6 can be achieved as outlined in Scheme 2, (step (h)), with various oxidizing agents such as oxalyl chloride/DMSO/amine base, TEMPO/NaOCl, TPAP/NMO, Jones reagent or many more under the appropriate conditions and temperatures and gives to compound of general formula A7. Subsequent epoxidation of A7 with e.g. trimethylsulfoxonium iodide in the presence of potassium tert-butoxide in DMSO as solvent (step (g)) gives then rise to compounds A8, as a mixture of the cis or (3α,6α) isomer and the trans or (3α,6β) respectively, readily separable from the mixture by chromatography or crystallization.

Scheme 2

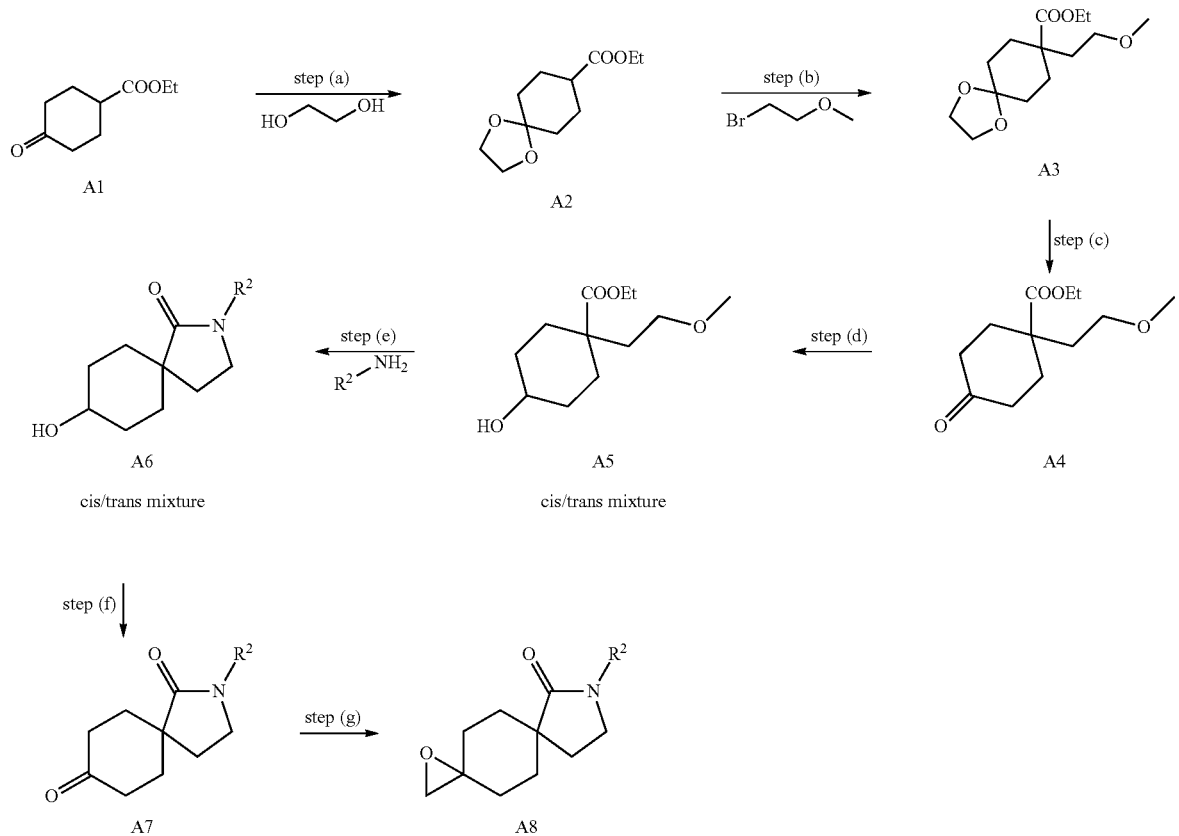

An alternative process to synthesize compounds A8 is described in scheme 3.

Scheme 3

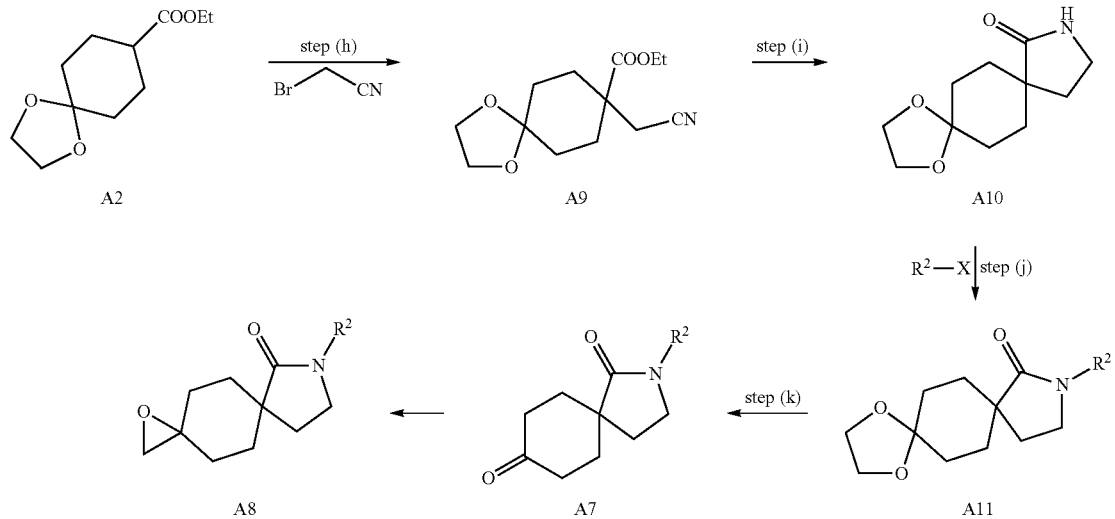

Starting from intermediate A2, this is alkylated with an α-haloacetonitrile in the presence of a suitable base such as LDA, NaH or the like in an appropriate solvent such as THF, diethylether or similar, with or without addition of HMPA, to provide compound A9 (step (h)). A9 is then further transformed to the lactam A10 by reduction of the nitrile group to the primary amine by, for example, catalytic hydrogenation with Raney-Ni as catalyst in NH3-EtOH as solvent and subsequent heating of the intermediate in toluene in the presence of a base such as triethylamine to achieve the ring closure reaction (step (i)).

Compounds of formula A11 can then be prepared from A10 and compounds of formula $R^2$—X, wherein X is halogen by making use of a Buchwald type copper- or palladium-catalysed coupling reaction (Buchwald et al. JACS, 2002, 124, p 7421). Suitable conditions for such reactions are for example: CuI and, for example, N,N'-dimethylethylenediamine as ligand and $K_3PO_4$ as base in a solvent such as DMF or with palladium(II) acetate as catalyst and, for example, bis(diphenylphosphino)-ferrocene (DPPF) as ligand, sodium tert-butoxide as a base in a solvent such as toluene.

Subsequently, compounds A11 can be converted to compounds A7 by acidic hydrolysis, for example by treatment with an aqueous mineral acid such as HCl, $H_2SO_4$ or the like (step (k)). The compounds of formula $R^2$—X are either commercial, known in the literature or were prepared following general synthetic procedures described in the art. Conversion of A7 to A8 is then accomplished as already described in scheme 2.

Also an embodiment of the present invention is a process to prepare a compound of formula (I) as defined above comprising the reaction of a compound of formula (II) in the presence of compound of formula (III);

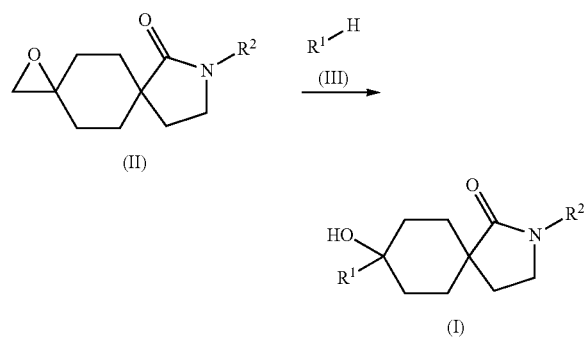

In particular in presence of a base, particularly sodium hydride and potassium tert-butoxide, in a solvent, particularly DMF, THF and tert-butanol, at a temperature comprised between RT and reflux, wherein $R^1$ and $R^2$ are as defined herein.

Also an object of the present invention is a compound according to formula (I) as described herein for use as therapeutically active substance.

Likewise an object of the present invention is a pharmaceutical composition comprising a compound according to formula (I) as described herein and a therapeutically inert carrier.

Also an object of the present invention is the use of a compound according to formula (I) as described herein for the treatment or prophylaxis of illnesses which are caused by disorders associated with the enzyme hormone-sensitive lipase.

The present invention relates to the use of a compound according to formula (I) as described above for the treatment or prophylaxis of diabetes, metabolic syndrome, dyslipidemia, atherosclerosis, obesity, cardiovascular diseases, myocardial dysfunction, inflammation, nonalkoholic fatty liver disease or nonalkoholic steatohepatitis The present invention particularly relates to the use of a compound according to formula (I) as described above for the treatment or prophylaxis of diabetes, metabolic syndrome, dyslipidemia, atherosclerosis or obesity.

A particular embodiment of the present invention is the use of a compound according to formula (I) as described above for the treatment or prophylaxis of diabetes.

A further particular embodiment of the present invention is the use of a compound according to formula (I) as described above for the treatment or prophylaxis of diabetes Type II.

Also an embodiment of the present invention is the use of a compound according to formula (I) as described above for the treatment or prophylaxis of cardiovascular diseases, myocardial dysfunction, inflammation, nonalkoholic fatty liver disease or nonalkoholic steatohepatitis.

A particular embodiment of the present invention is the use of a compound according to formula (I) as described above for the treatment or prophylaxis of nonalkoholic fatty liver disease or nonalkoholic steatohepatitis.

The present invention also relates to the use of a compound according to formula (I) as described above for the preparation of a medicament for the treatment or prophylaxis of diabetes, metabolic syndrome, dyslipidemia, atherosclerosis, obesity, cardiovascular diseases, myocardial dysfunction, inflammation, nonalkoholic fatty liver disease or nonalkoholic steatohepatitis.

The present invention particularly relates to the use of a compound according to formula (I) as described above for the preparation of a medicament for the treatment or prophylaxis of diabetes, metabolic syndrome, dyslipidemia, atherosclerosis or obesity.

A particular embodiment of the present invention is the use of a compound according to formula (I) as described above for the preparation of medicaments for the treatment or prophylaxis of diabetes.

A further particular embodiment of the present invention is the use of a compound according to formula (I) as described above for the preparation of medicaments for the treatment or prophylaxis of diabetes Type II.

Also an embodiment of the present invention is the use of a compound according to formula (I) as described above for the preparation of a medicament for the treatment or prophylaxis of cardiovascular diseases, myocardial dysfunction, inflammation, nonalkoholic fatty liver disease or nonalkoholic steatohepatitis.

A particular embodiment of the present invention is the use of a compound according to formula (I) as described above for the preparation of a medicament for the treatment or prophylaxis of nonalkoholic fatty liver disease or nonalkoholic steatohepatitis.

The present invention particularly relates to a compound according to formula (I) as described above for the treatment or prophylaxis of diabetes, metabolic syndrome, dyslipidemia, atherosclerosis, obesity, cardiovascular diseases, myocardial dysfunction, inflammation, nonalkoholic fatty liver disease or nonalkoholic steatohepatitis.

A particular embodiment of the present invention is a compound according to formula (I) as described above for the treatment or prophylaxis of diabetes, metabolic syndrome, dyslipidemia, atherosclerosis or obesity.

A further particular embodiment of the present invention is a compound according to formula (I) as described above for the treatment or prophylaxis of diabetes.

Also a further particular embodiment of the present invention is a compound according to formula (I) as described above for the treatment or prophylaxis of diabetes Type II.

Also a particular embodiment of the present invention is a compound according to formula (I) as described above for the treatment or prophylaxis of cardiovascular diseases, myocardial dysfunction, inflammation, nonalkoholic fatty liver disease or nonalkoholic steatohepatitis.

A further particular embodiment of the present invention is a compound according to formula (I) as described above for the treatment or prophylaxis of nonalkoholic fatty liver disease or nonalkoholic steatohepatitis.

Also an object of the invention is a method for the treatment or prophylaxis of diabetes, metabolic syndrome, dyslipidemia, atherosclerosis, obesity, cardiovascular diseases, myocardial dysfunction, inflammation, nonalkoholic fatty liver disease or nonalkoholic steatohepatitis, which method comprises administering an effective amount of a compound according to formula (I) as described above.

Also a particular object of the invention is a method for the treatment or prophylaxis of diabetes, metabolic syndrome, dyslipidemia, atherosclerosis or obesity, which method comprises administering an effective amount of a compound according to formula (I) as described above.

A particular embodiment of the present invention is a method for the treatment or prophylaxis of diabetes, which method comprises administering an effective amount of a compound according to formula (I) as described above.

A further particular embodiment of the present invention is a method for the treatment or prophylaxis of diabetes Type II, which method comprises administering an effective amount of a compound according to formula (I) as described above.

Also an embodiment of the present invention is a method for the treatment or prophylaxis of cardiovascular diseases, myocardial dysfunction, inflammation, nonalkoholic fatty liver disease or nonalkoholic steatohepatitis, which method comprises administering an effective amount of a compound according to formula (I) as described above.

Also a further embodiment of the present invention is a method for the treatment or prophylaxis of nonalkoholic fatty liver disease or nonalkoholic steatohepatitis, which method comprises administering an effective amount of a compound according to formula (I) as described above.

A further object of the present invention comprises a compound according to formula (I) as described herein, when manufactured according to any one of the described processes.

Assay Procedures

Production of Human Full Length Hormone Sensitive Lipase-His$^6$:
1) Cloning: cDNA was prepared from commercial human brain polyA+ RNA and used as a template in overlapping PCR to generate a full length human HSL ORF with a 3'-His6 tag. This full length insert was cloned into the pFast-BAC vector and the DNA-sequence of several single clones was verified. DNA from a correct full length clone with the 3'His6 tag was used to transform the *E. coli* strain DH10BAC. Resulting bacmid DNA was used to generate a titered baculovirus stock for protein generation. The sequence of the encoded HSL conforms to Swissprot entry Q05469, with the additional C-terminal His6-tag.

2) Protein purification: Culture: 5.5 L, High 5 cells expressing human full length HSL-His$^6$, 48 hr., containing 25 μM E–64. Cell count: $1.78 \times 10^{10}$ cells/ml, 90% viable.

Cells were thawed. On ice, cells were suspended in Base Buffer containing 10% glycerol, 25 mM Tris-Cl, 300 mM NaCl, 10 mM imidazole, 10 mM 2-mercaptoethanol, 2 μg pepstatin/ml, 2 μg leupeptin/ml, 2 μg antipain/ml, pH 8.0 at 4° C. in a final volume of 475 ml with $3.75 \times 10^7$ cells/ml. Sanitation was done at 3×30 sec., Lubrol PX was added to 0.2% final concentration followed by stirring for 15 min at 4° C. and centrifugation at 25 k×g, 60 min, 4° C. Soluble proteins were mixed with 60 ml of pre-washed and equilibrated Ni-NTA Agarose (Qiagen 30210) followed by tumbling end-over-end, 45 min., 4° C., centrifugation 1000 rpm 5 min and letting resin settle 5 min. Supernatant was removed, the resin washed in the centrifuge vessel using 5 volumes of Base Buffer containing 0.2% Lubrol PX. Centrifugation was done again, then the supernatant discarded. The resin was poured onto a 0.8 μm membrane in a disposable filter unit (Nalge 450-0080), and washed with 5 volumes of Base Buffer containing 0.2% Lubrol PX. It was then washed with 30 volumes of Base Buffer containing 60 mM imidazole pH 7.5 at 4° C. The protein was eluated with 5 volumes of 25 mM Tris-Cl, 300 mM NaCl, 200 mM imidazole, 10 mM 2-mercaptoethanol, pH 7.5 at 4° C. by tumbling resin with buffer end-over-end, 30 min., 4° C. The resin was captured on a 0.2 μm membrane disposable filter unit (Millipore SCGP U02 RE) and the eluate collected in the reservoir. The eluate was concentrated using a 30 k MWCO centrifugal filter device (Sartorius Vivascience Vivacell 100, VC1022), to 20 ml. It was then dialyzed overnight at 4° C., two times against 2 L of 10% glycerol, 25 mM Tris-Cl, 300 mM NaCl, 0.2 mM EDTA, 0.2 mM DTT, pH 7.5 at 4° C. The protein was filtered using a 0.22 μm disposable filter unit (Millipore SCGP00525). The protein concentration was calculated from absorbance at 280 nm, using $280=0.67$ cm$^{-1}$ mg-1. Yield was 235 mg, total. The protein was stored at –80° C.

Human Hormone-Sensitive Lipase (HSL) Enzyme Inhibition Assay:

HSL enzyme activity was measured by a colorimetric assay using 2,3-dimercapto-1-propanol tributyrate (Aldrich, St. Louis, Mo.) as a substrate. Typically, 1.5 mM 2,3-dimercapto-1-propanol tributyrate (DMPT) in 100 mM MOPS, pH 7.2, 0.2 mg/ml fatty acid-free BSA was prepared by sonication at 4° C. to homogenous suspension. Test compounds (2 mM stock in DMSO) were diluted 3 fold in series in DMSO. Compound solutions were diluted 24 fold in 1.5 mM DMPT containing solution and 18 ul per well was added to 384-well microplates (Corning Costar). Twelve microliters per well of human HSL (15 ug/ml) was added and the reaction mixture was incubated at 37° C. for 20 minutes. Six microliters of 12 mM dithio-bis-(2-nitrobenzoic acid) (DTNB) in DMSO plus 1.2% SDS and 0.6% Triton X-100 were added and the mixture was incubated at room temperature for 15 minutes. Product production was monitored by reading absorbance at 405 nm on an Envision Reader (PerkinElmer Life and Analytical Sciences, Shelton, Conn.).

Cellular Assay:

The following assay was used to measure the effect of the compounds to inhibit lipolysis in intact cells (adipocytes).

3T3-L1 pre-adipocyte cells were plated into 96-well plates at a density of 20,000 cells/well in 200 ul growth media (DMEM/10% Calf Serum/1× antibiotic-antimycotic) until confluent. At 48 hours post-confluency, the medium was removed and the cells were differentiated into adipocytes with differentiation medium (DMEM/10% FBS/1× Antibiotic-Antimycotic PLUS: 1 uM IBMX (3-Isobutyl-1-methylxanthine) Inhibitor of phosphodiesterases, 1 uM Dexamethasone, 1 uM Rosiglitazone, 10 ug/ml Insulin). The cells were incubated in said medium for 3 days and then medium was changed to post-differentiation medium (DMEM/10% FBS PLUS: 10 ug/ml Insulin) and the cells were incubated for an additional 3 days. The medium was then changed to maintenance media (DMEM/10% FBS). The cells were fed every 3 days with maintenance media until use. The lipolysis assay may be performed on day 9-14 after the initiation of differentiation in 96 well plates.

The lipolysis assay was performed as follows. The adipocytes were washed 2× with 200 ul Krebs Ringer Bicarbonate Hepes buffer (KRBH)/3% BSA. Test compounds were at 10 mM in DMSO and were initially diluted to 5 mM in DMSO. They were then serially diluted 5-fold in DMSO (5 mM to 320 pM). Each compound was then diluted 200-fold into KRBH/3% BSA (0.5% DMSO final). The resulting solutions range from 25 uM to 1.6 pM final. One hundred fifty ul of the diluted compounds were added to each well (in triplicate) and the cells were preincubated 30 min at 37° C. Forskolin (50 uM final) was added to the wells and the cells were incubated 120 minutes at 37° C. One hundred ul was collected into a new 96-well plate for glycerol analysis. The amount of glycerol produced was determined using a glycerol determination kit (Sigma).

| Examples | HSL hum IC50 (uM) |
|---|---|
| 1 | 0.0077 |
| 2 | 0.0681 |
| 3 | 0.0509 |
| 4 | 0.0274 |
| 5 | 0.0163 |
| 6 | 0.264 |
| 7 | 0.0137 |
| 8 | 0.213 |
| 9 | 0.0306 |
| 10 | 0.0418 |
| 11 | 0.01 |
| 12 | 0.037 |

Compounds of formula (I) and their pharmaceutically acceptable salts or esters thereof as described above have $IC_{50}$ values between 0.0001 uM and 1000 uM, particular compounds have $IC_{50}$ values between 0.001 uM and 500 uM, further particular compounds have $IC_{50}$ values between 0.001 uM and 5 uM. These results have been obtained by using the foregoing HSL enzyme inhibition assay (uM means micro-Molar).

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula (I) and their pharmaceutically acceptable salts can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given herein can be exceeded when this is shown to be indicated. The invention is illustrated hereinafter by Examples, which have no limiting character.

In case the preparative examples are obtained as a mixture of enantiomers, the pure enantiomers can be separated by methods described herein or by methods known to the man skilled in the art, such as e.g. chiral chromatography or crystallization.

EXAMPLES

Example 1

(5α,8α)-8-hydroxy-8-((2-oxopyrrolidin-1-yl)methyl)-2-(4-(trifluoromethyl)phenyl)-2-azaspiro[4.5]decan-1-one

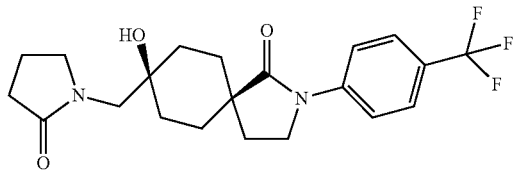 [SMILES: O=C1CCCN1C[C@]1(O)CC[C@]2(CCN(c3ccc(C(F)(F)F)cc3)C2=O)CC1]

Step 1: 1,4-Dioxa-spiro[4.5]decane-8-carboxylic acid ethyl ester

Ethyl-cyclohexanone-4-carboxylate (54.8 g) was dissolved in toluene (120 ml). Then, ethylene glycol (24.8 ml) and toluene-4-sulfonic acid monohydrate (612 mg) were added to the reaction mixture. The mixture was refluxed over night and water was removed azeotropically with a Dean-Stark apparatus. The reaction mixture was cooled, poured into ice/water and basified with 2M aqueous NaOH to pH 9. The aqueous layer was extracted two times with ethyl acetate. The combined organic layers were washed with brine, dried over $Na_2SO_4$, filtered and the solvent was evaporated. The residue was purified by flash chromatography (silica gel, gradient of heptane in ethyl acetate) to give the title compound as a light yellow liquid (39.5 g). MS (m/e)=215.3 [MH+].

Step 2: 8-Cyanomethyl-1,4-dioxa-spiro[4.5]decane-8-carboxylic acid ethyl ester To a stirred solution of diisopropylamine (10.09 ml, 69.76 mmol) in THF (150 ml) was added nBuLi (1.9 M solution in hexane, 26.09 ml, 51.1 mmol) drop wise at −40° C. followed by HMPA (31.0 ml, 178.0 mmol) under nitrogen atmosphere, and the reaction mixture was stirred for 30 minutes at −40° C. It was then cooled further to −78° C., and a solution of 1,4-dioxa-spiro[4.5]decane-8-carboxylic acid ethyl ester (10 g, 46.5 mmol) in THF (20 ml) was added keeping the temperature below −70° C. throughout the addition. After stirring for 25 min at −78° C., bromoacetonitrile (3.8 ml, 55.8 mmol) was added slowly, and the reaction mixture was then allowed to warm to 25° C. The mixture was poured into cold water (100 ml) and the aqueous layer was extracted with EtOAc (5×70 ml). The combined organic layer was washed successively with saturated aqueous solution of NH4Cl (3×50 ml), H2O (2×50 ml) and then with brine (1×40 ml), dried (Na2SO4), filtered and evaporated in vacuo. The crude compound obtained was purified by column chromatography over silica gel (22-25% EtOAc/hexane) to give the title compound (6 g) as a pale yellow liquid. MS (m/e): 254.2 [MH+].

Step 3: 1,4-Dioxa-10-aza-dispiro[4.2.4.2]tetradecan-9-one

To a stirred solution of 8-cyanomethyl-1,4-dioxa-spiro[4.5]decane-8-carboxylic acid ethyl ester (12 g, 47.3 mmol) in a mixture of NH3-EtOH (200 ml, 7:93) was added Raney-Ni (4.16 g, 70.95 mmol) under nitrogen atmosphere at 25° C. The reaction mixture was then hydrogenated at 40° C. in an autoclave under 400 psi H2 pressure for 16 h. After the completion of reaction, the mixture was filtered through a bed of celite, and the filtrate was evaporated under reduced pressure. The crude material thus obtained (10 g, 38.9 mmol) was dissolved in dry toluene (100 ml) and to the stirred solution was added Et3N (10 ml, 71.14 mmol) under a nitrogen atmosphere at 25° C. The mixture was then heated under reflux for 24 h. After the completion of reaction, it was cooled to 25° C., the precipitated white solid was filtered, washed with hexane (3×50 ml), dried under vacuum to give the title compound (7.3 g) as a white solid. MS (m/e): 212.2 [MH+].

Step 4: 10-(4-Trifluoromethyl-phenyl)-1,4-dioxa-10-aza-dispiro[4.2.4.2]tetradecan-9-one

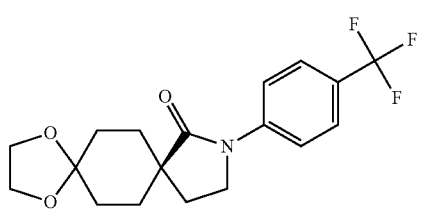

1,4-Dioxa-10-aza-dispiro[4.2.4.2]tetradecan-9-one (4 g) was dissolved in DMF (189 ml) at RT under an argon atmosphere. Then, 1-bromo-4-(trifluoromethyl)benzene (6.39 g), N,N′-dimethylethylenediamine (sym) (3.34 g), cuprous iodide (5.41 g) and K3PO4 (7.13 g) were added and the mixture was heated at 100° C. for 12 hours. The reaction mixture was cooled to RT, filtered and saturated aqueous NH4Cl solution was added. The mixture was then extracted twice with AcOEt, the combined organic layers were washed with brine, dried over Na2SO4, filtered and the solvent was evaporated off in vacuo. The crude product was purified by flash chromatography (silica gel, gradient of 0% to 25% of acetonitrile in CH2Cl2) to give the title compound as white crystalline solid (4 g). MS (m/e): 356.146 [MH+].

Step 5: 2-(4-Trifluoromethyl-phenyl)-2-aza-spiro[4.5]decane-1,8-dione

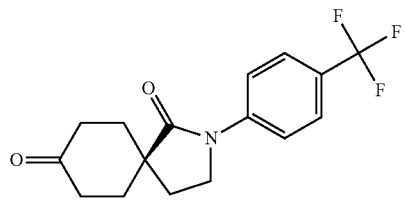

10-(4-Trifluoromethyl-phenyl)-1,4-dioxa-10-aza-dispiro[4.2.4.2]tetradecan-9-one (6.7 g) was dissolved in tetrahydrofuran (189 ml) aqueous hydrochloric acid solution (2M, 94.3 ml) was added and the mixture was stirred for 12 hours at RT. The reaction mixture was poured into ice/water and extracted twice with ethyl acetate. The combined organic layers were washed with brine, dried over Na2SO4, filtered and the solvent was evaporated to give the title compound as a colorless foam (4.9 g). MS (m/e): 311 [M+].

Step 6: (3α,6α)-8-(4-Trifluoromethyl-phenyl)-1-oxa-8-aza-dispiro[2.2.4.2]dodecan-7-one

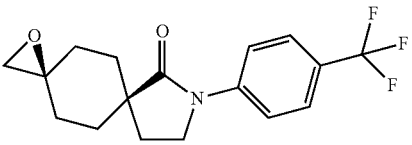 [SMILES: O=C1N(c2ccc(C(F)(F)F)cc2)CC[C@]12CC[C@]1(CC2)CO1]

2-(4-Trifluoromethyl-phenyl)-2-aza-spiro[4.5]decane-1,8-dione (4.9 g) and trimethylsulfoxonium iodide (5.37 g) were dissolved in DMSO (28.8 ml). Then, a solution of potassium tert-butoxide (2.74 g) in DMSO (28.8 ml) was added and the mixture was stirred at RT for 12 hours. The reaction mixture was poured into ice/water and was extracted twice with ethyl acetate. The combined organic layers were washed with brine, dried over Na2SO4 and filtered. The solvent was evaporated and the residue was purified by flash chromatography (silica gel, gradient 0% to 50% AcOEt in heptane in) to give the title compound as a white solid (3.816 g). MS (m/e): 326.2 [MH+]

Step 7: (5α,8α)-8-hydroxy-8-((2-oxopyrrolidin-1-yl)methyl)-2-(4 (trifluoromethyl)phenyl)-2-azaspiro[4.5]decan-1-one To a suspension of sodium hydride (69.7 mg) in DMF (5.25 mL) at 0° C. was added under an argon atmosphere 2-pyrrolidone (52.3 mg) and the reaction mixture was stirred for 10 minutes. A solution of (3α,6α)-8-(4-trifluoromethyl-phenyl)-1-oxa-8-aza-dispiro[2.2.4.2]dodecan-7-one (200 mg, product of example 1 step 6) in DMF (2 ml) was added and the reaction mixture heated at 110° C. for 12 h. The reaction mixture was poured into water, extracted with EtOAc, washed with brine and dried over Na$_2$SO$_4$ and concentrated in vacuo to give a crude residue which was purified by flash column chromatography (silica gel, gradient of 0% to 50% EtOAc in heptane) to yield the title compound as a white solid (113 mg). MS (m/e): 411.188 (MH$^+$).

Example 2

8-Hydroxy-8-(2-oxo-piperidin-1-ylmethyl)-2-(4-trifluoromethyl-phenyl)-2-aza-spiro[4.5]decan-1-one

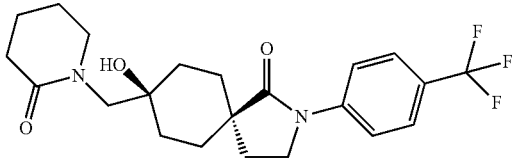 [SMILES: O=C1CCCCN1C[C@]1(O)CC[C@]2(CCN(c3ccc(C(F)(F)F)cc3)C2=O)CC1]

The title compound was prepared in analogy to example 1 step 7 from (3α,6α)-8-(4-trifluoromethyl-phenyl)-1-oxa-8-aza-dispiro[2.2.4.2]dodecan-7-one (product of example 1 step 6) and 2-piperidinone as a white solid. MS (m/e): 425.204 [MH$^+$].

Example 3

(5α,8α)-8-hydroxy-2-(4-isopropoxyphenyl)-8-((2-oxopyrrolidin-1-yl)methyl)-2-azaspiro[4.5]decan-1-one

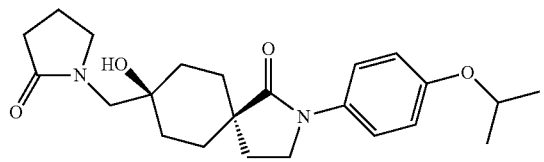 [SMILES: CC(C)Oc1ccc(N2CC[C@]3(CC[C@@](O)(CN4CCCC4=O)CC3)C2=O)cc1]

Step 1: 1,4-Dioxa-spiro[4.5]decane-8-carboxylic acid ethyl ester

Ethyl-cyclohexanone-4-carboxylate (54.8 g) was dissolved in toluene (120 ml). Then, ethylene glycol (24.8 mL) and toluene-4-sulfonic acid monohydrate (612 mg) were added to the reaction mixture. The mixture was refluxed over night and water was removed azeotropically with a Dean-Stark apparatus. The reaction mixture was cooled, poured into ice/water and basified with 2M aqueous NaOH to pH 9. The aqueous layer was extracted two times with ethyl acetate. The combined organic layers were washed with brine, dried over Na$_2$SO$_4$, filtered and the solvent was evaporated. The residue was purified by flash chromatography (silica gel, gradient of heptane in ethyl acetate) to give the title compound as a light yellow liquid (39.5 g). MS (m/e)=215.3 [MH$^+$].

Step 2: 1-(2-Methoxy-ethyl)-4-oxo-cyclohexanecarboxylic acid ethyl ester

A solution of 1,4-dioxa-spiro[4.5]decane-8-carboxylic acid ethyl ester (39.5 g) in THF (200 ml) was added dropwise over a period of 45 minutes at −5° C. (ice/methanol bath) to a solution of lithiumdiisopropylamide (2M in THF, 184.3 mL) in THF (300 ml). Stirring was continued for 2.5 hours at 0° C. The reaction mixture was cooled to −5° C. and 2-bromoethyl-methylether (34.6 ml) was added dropwise over a period of 30 minutes. Stirring was continued for 12 hours at RT. The reaction mixture was cooled to 0° C. and aqueous HCl (25%, 300 ml) was added dropwise over a period of 45 minutes to pH 1. Stirring was continued for 2 hours at RT. The reaction mixture was poured into ice/water and extracted two times with ethyl acetate. The combined organic layers were washed with brine, dried over Na$_2$SO$_4$, filtered and the solvent was evaporated. The residue was purified by flash chromatography (silica gel, gradient of heptane in ethyl acetate) to give the title compound as a yellow liquid (25.2 g). MS (EI)=288.0 [M$^+$].

Step 3: 4-1-(2-methoxy-ethyl)-cyclohexanecarboxylic acid ethyl ester 1-(2-Methoxy-ethyl)-4-oxo-cyclohexanecarboxylic acid ethyl ester (50 g) was dissolved in 2-propanol (400 ml). The mixture was cooled to 0° C. and sodium borohydride (10 g) was added in 8 portions over 20 minutes. Stirring was continued for 2 hours at 0° to 6° C. The reaction mixture was partitioned between ice/water which was saturated with brine and ethyl acetate, the layers were separated and the aqueous layer further extracted with AcOEt. The combined organic layers were washed with brine, dried over Na$_2$SO$_4$, filtered and the solvent was evaporated off. The title compound was obtained as a mixture of cis and trans diastereomeres (ratio: 3/1) as a yellow oil (41.7 g) and was used without further purification. MS (EI)=230.0 [M$^+$].

Step 4: 8-Hydroxy-2-(4-isopropoxy-phenyl)-2-aza-spiro[4.5]decan-1-one

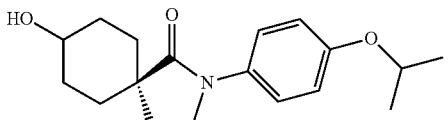

4-Isopropoxy-phenylamine (11.3 g) was added to a solution of 4-hydroxy-1-(2-methoxy-ethyl)-cyclohexanecarboxylic acid ethyl ester (11.5 g) in toluene (361 ml). The mixture was stirred for 10 minutes at RT. Then, dimethylaluminiumchloride (0.9 M in hexane, 99 ml) was added dropwise and the reaction mixture was heated to reflux for 4 h. The mixture was then cooled to 0° C., water (50 ml) was added dropwise then AcOEt (300 ml). The mixture was stirred further 30 minutes, more AcOEt was added, the layers were then separated, the organic layer was dried over MgSO4, filtered and the solvent was evaporated off. The crude product was triturated with diethyl ether/heptane to give the title compound as a mixture of cis/trans isomers as brown solid (14.3 g) which was used directly in the next step. MS (m/e): 304.190 [MH$^+$].

Step 5: 2-(4-Isopropoxy-phenyl)-2-aza-spiro[4.5]decane-1,8-dione

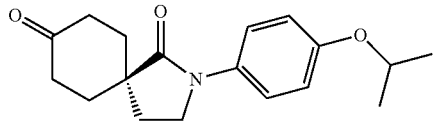

To a solution of 8-hydroxy-2-(4-isopropoxy-phenyl)-2-aza-spiro[4.5]decan-1-one (7 g) and 2,2,6,6-tetramethylpiperidine-1-oxyl (721 mg) in dichloromethane (250 ml) were added sequentially a solution of potassium bromide (549 mg) in water (60 ml), sodium hypochlorite (52.8 ml), sodium bicarbonate (5.81 g) and the reaction mixture was then stirred for 3 hour at RT. The reaction mixture was poured into ice/water and extracted three times with CH$_2$Cl$_2$. The combined organic layers were washed with brine, dried over Na$_2$SO$_4$, filtered and the solvent was evaporated off. The residue was purified by flash chromatography (silica gel, gradient 0% to 50% ethyl acetate in heptane) to give the title compound as a brown solid (5 g). MS (m/e): 302.174 [MH$^+$].

Step 6: (3α,6α)-8-(4-Isopropoxy-phenyl)-1-oxa-8-aza-dispiro[2.2.4.2]dodecan-7-one

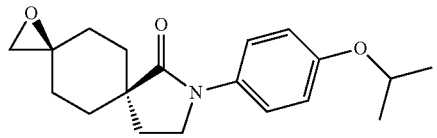 [SMILES: CC(C)Oc1ccc(N2CC[C@]3(CC[C@]4(CC3)CO4)C2=O)cc1]

2-(4-Isopropoxy-phenyl)-2-aza-spiro[4.5]decane-1,8-dione (3 g) and trimethylsulfoxonium iodide (3.4 g) were dissolved in DMSO (72 ml). Then, a solution of potassium tert-butoxide (1.73 g) in DMSO (72 ml) was added and the mixture was stirred at RT for 12 hours. The reaction mixture was poured into ice/water and was extracted twice with ethyl acetate. The combined organic layers were washed with brine, dried over Na$_2$SO$_4$ and filtered. The solvent was evaporated and the residue was purified by flash chromatography (silica gel, gradient 0% to 50% AcOEt in heptane in) to give the title compound as a white solid (2.06 g). MS (m/e): 316.190 [MH$^+$].

Step 7: (5α,8α)-8-hydroxy-2-(4-isopropoxyphenyl)-8-(2-oxopyrrolidin-1-yl)methyl)-2-azaspiro[4.5]decan-1-one The title compound was prepared in analogy to example 1 step 7 from (3α,6α)-8-(4-isopropoxy-phenyl)-1-oxa-8-aza-dispiro[2.2.4.2]dodecan-7-one and 2-pyrrolidone as an off white solid. MS (m/e): 401.242 [MH$^+$].

Example 4

(5α,8α)-8-Hydroxy-2-(4-isopropoxyphenyl)-8-((2-oxopiperidin-1-yl)methyl)-2-azaspiro[4.5]decan-1-one

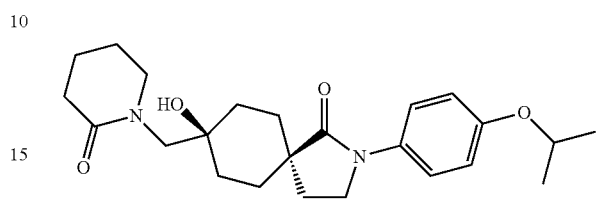

The title compound was prepared in analogy to example 1 step 7 from (3α,6α)-8-(4-isopropoxy-phenyl)-1-oxa-8-aza-dispiro[2.2.4.2]dodecan-7-one (product of example 3 step 6) and 2-piperidinone as a white solid. MS (m/e): 415.258 [MH$^+$].

Example 5

(5α,8α)-8-(2,2-Difluoro-ethoxymethyl)-8-hydroxy-2-(4-isopropoxy-phenyl)-2-aza-spiro[4.5]decan-1-one

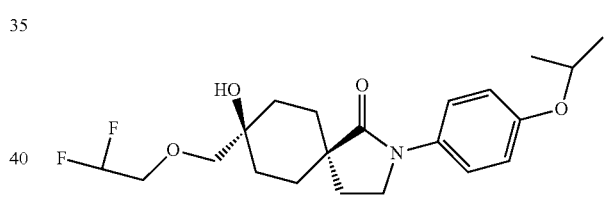

The title compound was prepared in analogy to example 1 step 7 from (3α,6α)-8-(4-isopropoxy-phenyl)-1-oxa-8-aza-dispiro[2.2.4.2]dodecan-7-one (product of example 3 step 6) and 2,2-difluoroethanol as a white solid. MS (m/e): 398.212 [MH$^+$].

Example 6

(5α,8α)-8-Hydroxy-2-(6-isopropoxy-pyridin-3-yl)-8-(2-oxo-pyrrolidin-1-ylmethyl)-2-aza-spiro[4.5]decan-1-one

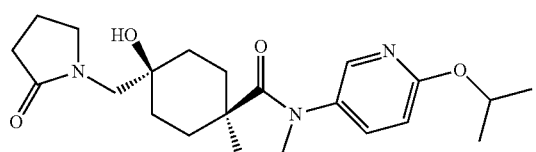

Step 1: 8-Hydroxy-2-(6-isopropoxy-pyridin-3-yl)-2-aza-spiro[4.5]decan-1-one

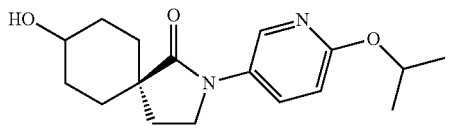

In analogy to example 3 step 4, from 6-isopropoxy-pyridin-3-ylamine (11.4 g), 4-hydroxy-1-(2-methoxy-ethyl)-cyclohexanecarboxylic acid ethyl ester (11.5 g) and dimethylaluminiumchloride (0.9 M in hexane, 99.9 ml) in toluene (360 ml) the title compound was obtained as mixture of cis/trans isomers as a light red solid (7.49 g). MS (m/e): 305.2 [MH$^+$].

Step 2: 2-(6-Isopropoxy-pyridin-3-yl)-2-aza-spiro[4.5]decane-1,8-dione

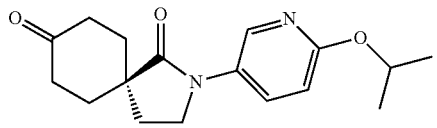

In analogy to example 3 step 5, by oxidation of 8-hydroxy-2-(6-isopropoxy-pyridin-3-yl)-2-aza-spiro[4.5]decan-1-one (4.5 g) the title compound (2.43 g) was obtained as yellow amorphous solid. MS (m/e): 303.169 [MH$^+$].

Step 3: (3α,6α)-8-(6-Isopropoxy-pyridin-3-yl)-1-oxa-8-aza-dispiro[2.2.4.2]dodecan-7-one

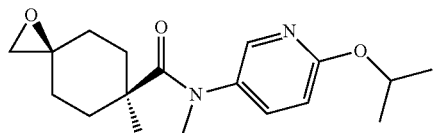

In analogy to example 3 step 6, by epoxidation of 2-(6-isopropoxy-pyridin-3-yl)-2-aza-spiro[4.5]decane-1,8-dione (2.5 g) the title compound (0.73 g) was obtained as yellow solid. MS (m/e): 317.184 [MH$^+$].

Step 4: (5α,8α)-8-Hydroxy-2-(6-isopropoxy-pyridin-3-yl)-8-(2-oxo-pyrrolidin-1-ylmethyl)-2-aza-spiro[4.5]decan-1-one The title compound was prepared in analogy to example 1 step 7 from (3α,6α)-8-(6-isopropoxy-pyridin-3-yl)-1-oxa-8-aza-dispiro[2.2.4.2]dodecan-7-one and 2-pyrrolidone as a light yellow solid. MS (m/e): 402.238 [MH$^+$].

Example 7

(5α,8α)-8-hydroxy-2-(6-isopropoxypyridin-3-yl)-8-((2,2,2-trifluoroethoxy)methyl)-2-azaspiro[4.5]decan-1-one

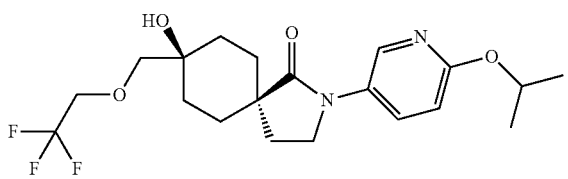 [SMILES: CC(C)Oc1ccc(N2CC[C@]3(CC[C@@](O)(COCC(F)(F)F)CC3)C2=O)cn1]

The title compound was prepared in analogy to example 1 step 7 from (3α,6α)-8-(6-isopropoxy-pyridin-3-yl)-1-oxa-8-aza-dispiro[2.2.4.2]dodecan-7-one, product of example 6 step 3, and 2,2,2-trifluoroethanol as an off white solid. MS (m/e): 417.199 [MH$^+$].

Example 8

(5α,8α)-8-Hydroxy-8-(2-oxo-pyrrolidin-1-ylmethyl)-2-[4-((R)-2,2,2-trifluoro-1-hydroxy-ethyl)-phenyl]-2-aza-spiro[4.5]decan-1-one

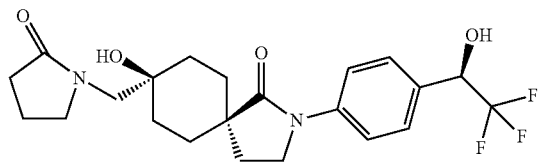 [SMILES: O=C1CCCN1C[C@]1(O)CC[C@]2(CCN(c3ccc([C@@H](O)C(F)(F)F)cc3)C2=O)CC1]

Step 1: 4-[(R)-1-(4-Bromo-phenyl)-2,2,2-trifluoro-ethoxymethyl]-phenol

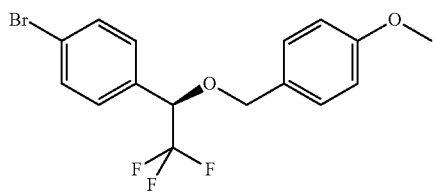 [SMILES: COc1ccc(CO[C@H](c2ccc(Br)cc2)C(F)(F)F)cc1]

(R)-1-(4-bromophenyl)-2,2,2-trifluoroethanol (3.5 g, synthesis described in J. Org. Chem. 2009, 74, 1605-1610) was dissolved in THF (50 ml) under an argon atmosphere, NaH (719 mg) was added at 0° C. followed by tetrabutylammonium iodide (507 mg) then 4-methoxy-benzylbromide (3.04 g) and the mixture was stirred for 3.5 h at 20° C.

The reaction was quenched with water (15 ml) and then 1N aqueous HCl (15 ml) was added followed by EtOAc (30 ml). The layers were separated and the aqueous layer was extracted twice with EtOAc (each 30 ml). The combined aqueous layers were washed with brine, dried over Na$_2$SO$_4$ and concentrated in vacuo. The residue was purified by flash chromatography (silica gel, gradient 0% to 25% ethyl acetate in heptane) to give the title compound as a white solid (4.7 g).
$^1$H-NMR (δ, CDCl$_3$): 7.55 (m, 2H), 7.3 (m, 2H), 7.2 (m, 2H), 6.88 (m, 2H), 4.63 (d, 1H, J=11.5 Hz), 4.58 (q, 1H, J=4.6 Hz), 4.38 (d, 1H, J=11.5 Hz), 3.82 (s, 3H).

Step 2: 10-{4-[(R)-2,2,2-Trifluoro-1-(4-methoxy-benzyloxy)-ethyl]-phenyl}-1,4-dioxa-10-aza-dispiro[4.2.4.2]tetradecan-9-one

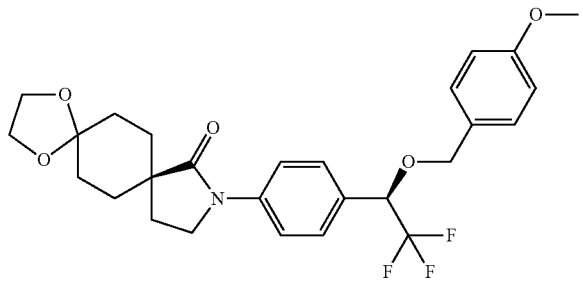

The title compound was prepared in analogy to example 1 step 4 from 1,4-dioxa-10-aza-dispiro[4.2.4.2]tetradecan-9-one (2.05 g) (described in example 1, step 3) and 4-[(R)-1-(4-bromo-phenyl)-2,2,2-trifluoro-ethoxymethyl]-phenol (4.66 g) as a white solid (4.9 g) which was directly used in the next step.

Step 3: 2-{4-[(R)-2,2,2-Trifluoro-1-(4-methoxy-benzyloxy)-ethyl]-phenyl}-2-aza-spiro[4.5]decane-1,8-dione

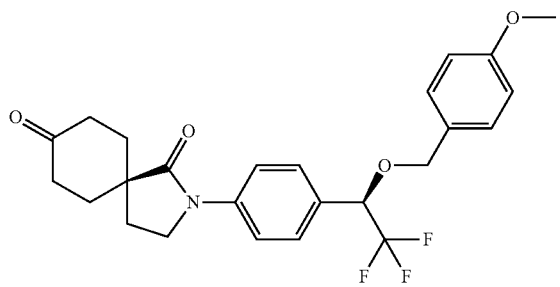

The title compound was prepared in analogy to example 1, step 5 from 10-{4-[(R)-2,2,2-trifluoro-1-(4-methoxy-benzyloxy)-ethyl]-phenyl}-1,4-dioxa-10-aza-dispiro[4.2.4.2]tetradecan-9-one (4.91 g) by treatment with 2 M HCl (58.3 ml) in THF (68.2 ml) as a white solid. (3.5 g).

Step 4: (3α,6α)-8-{4-[(R)-2,2,2-Trifluoro-1-(4-methoxy-benzyloxy)-ethyl]-phenyl}-1-oxa-8-aza-dispiro[2.2.4.2]dodecan-7-one

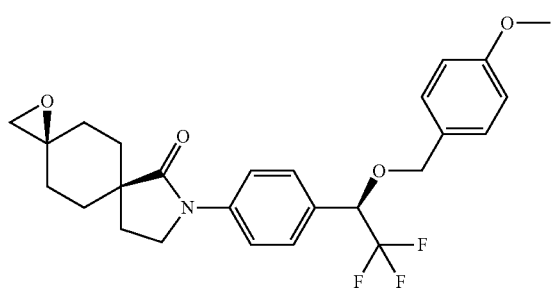 [SMILES: COc1ccc(CO[C@H](c2ccc(N3CC[C@]4(CC[C@]5(CC4)CO5)C3=O)cc2)C(F)(F)F)cc1]

In analogy to example 1 step 6 by epoxidation of 2-{4-[(R)-2,2,2-trifluoro-1-(4-methoxy-benzyloxy)-ethyl]-phenyl}-2-aza-spiro[4.5]decane-1,8-dione (2.5 g) the title compound (2 g) was obtained as yellow solid. MS (m/e): 476.2 [MH⁺].

Step 5: (5α,8α)-8-Hydroxy-8-(2-oxo-pyrrolidin-1-ylmethyl)-2-{4-[(R)-2,2,2-trifluoro-1-(4-methoxy-benzyloxy)-ethyl]-phenyl}-2-aza-spiro[4.5]decan-1-one

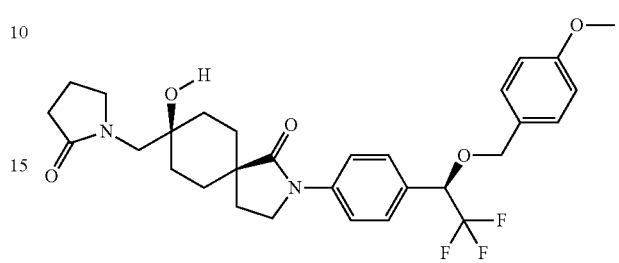

To a solution of (3α,6α)-8-{4-[(R)-2,2,2-trifluoro-1-(4-methoxy-benzyloxy)-ethyl]-phenyl}-1-oxa-8-aza-dispiro[2.2.4.2]dodecan-7-on (250 mg) and pyrrolidin-2-one (58.2 mg) in a mixture of t-butylalcohol (5 ml) and THF (2 ml) was added potassium tert-butoxide (47.2 mg) and the mixture was stirred at 80° C. for 12 h. The solvent was removed in vacuo, the residue was taken up in EtOAc which was then washed with water, brine and dried over MgSO₄. The solvent was evaporated off and the residue was purified by flash chromatography (silica gel, gradient 0% to 5% MeOH in methylen chloride) to give the title compound as a white solid (134 mg). MS (m/e)=561.3 [MH⁺].

Step 6: (5α,8α)-8-Hydroxy-8-(2-oxo-pyrrolidin-1-ylmethyl)-2-[4-((R)-2,2,2-trifluoro-1-hydroxy-ethyl)-phenyl]-2-aza-spiro[4.5]decan-1-one (5α,8α)-8-Hydroxy-8-(2-oxo-pyrrolidin-1-ylmethyl)-2-{4-[(R)-2,2,2-trifluoro-1-(4-methoxy-benzyloxy)-ethyl]-phenyl}-2-aza-spiro[4.5]decan-1-one (134 mg) was dissolved in methylene chloride (5 ml), water (0.25 ml) was added followed by DDQ (163 mg) and the reaction mixture was stirred for 18 h at RT. The mixture was then partitioned between aqueous KHCO₃ and methylene chloride, the layers were separated and the organic layer was washed with aqueous KHCO₃ then with brine, dried over MgSO₄, filtered and concentrated in vacuo. The residue was purified by flash chromatography (silica gel, gradient 0% to 5% MeOH in methylen chloride) to give the title compound as a white solid (134 mg). MS (m/e)=441.3 [MH⁺].

Example 9

(5α,8α)-8-Hydroxy-8-((2-oxopyrrolidin-1-yl)methyl)-2-(4-((R)-1,1,1-trifluoropropan-2-yloxy)phenyl)-2-azaspiro[4.5]decan-1-one

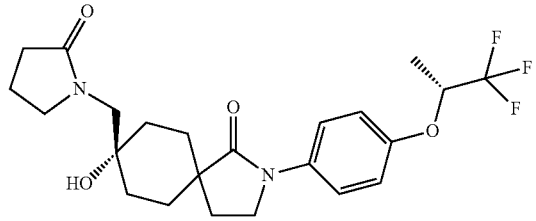

Step 1: 4-((R)-2,2,2-Trifluoro-1-methyl-ethoxy)-phenylamine

Sodium hydride (55%, 3.22 g) was added to DMF (20 mL) and the mixture was cooled to 0° C. Then, (R)-1,1,1-trifluoro-2-propanol (8.5 g) [CAS 17628-73-8] was added over a period of 1 h and stirring was continued for 30 minutes at 0° C. A solution of 1-fluoro-4-nitro-benzene [CAS 350-46-9] (10 g) in DMF (15 mL) was added over a period of 1.5 h while the internal temperature was kept between 5 to 15° C. Following addition, the mixture was allowed to warm to RT and stirring was continued for another 12 h. The reaction mixture was acidified and partitioned between ethyl acetate and water. The organic layer was separated, dried over $Na_2SO_4$ and evaporated to dryness. The residue was dissolved in methanol (150 ml) and Pd on carbon (10% Pd, 1 g) was added. The mixture was then hydrogenated at RT for 12 hours. The catalyst was removed by filtration and the filtrate was concentrated in vacuo to provide crude 4-((R)-2,2,2-trifluoro-1-methyl-ethoxy)-phenylamine as a dark liquid (14.5 g). MS (m/e): 206.1 ($MH^+$).

Step 2: 8-Hydroxy-2-[4-((R)-2,2,2-trifluoro-1-methyl-ethoxy)-phenyl]-2-aza-spiro[4.5]decan-1-one (mixture of cis and trans diastereomers)

4-((R)-2,2,2-Trifluoro-1-methyl-ethoxy)-phenylamine (7.57 g,) was added to a solution of 4-hydroxy-1-(2-methoxy-ethyl)-cyclohexanecarboxylic acid ethyl ester (5.0 g, obtained in example 3, step 3) in toluene (150 ml). The mixture was stirred for 10 minutes at RT. Then, dimethylaluminiumchloride (1M in hexane, 65.1 mL) was added dropwise over a period of 45 minutes. The reaction mixture was heated to reflux for 2 h and was then kept at 95° C. for 16 h. The mixture was cooled, poured into ice/water and extracted two times with ethyl acetate. The combined organic layers were washed with brine, dried over $Na_2SO_4$, filtered and the solvent was evaporated. The title compound was obtained as an mixture of cis and trans diastereomers as a light brown solid (5.79 g). This mixture was used without further purification. MS (m/e): 358.3 [$MH^+$].

Step 3: 2-[4-((R)-2,2,2-trifluoro-1-methyl-ethoxy)-phenyl]-2-aza-spiro[4.5]decane-1,8-dione To a solution of 8-hydroxy-2-[4-((R)-2,2,2-trifluoro-1-methyl-ethoxy)-phenyl]-2-aza-spiro[4.5]decan-1-one (5.79 g) and 2,2,6,6-tetramethylpiperidine-1-oxyl radical (TEMPO) (506 mg) in $CH_2Cl_2$ (85 ml) was added a solution of potassium bromide (482 mg) in water (16 mL). Then, sodiumhypochlorite (13%, 42.5 mL) was added dropwise over a period of 10 minutes followed by sodium bicarbonate ($NaHCO_3$) (4.08 g). The mixture was stirred for 1.5 h at RT. TLC showed a remainder of starting material. More TEMPO (125 mg) and sodiumhypochlorite solution (10 mL) were added to the reaction mixture and the mixture was stirred for additional 2 h at RT. The reaction mixture was poured into ice/water and was extracted three times with $CH_2Cl_2$. The combined organic layers were washed with brine, dried over $Na_2SO_4$, filtered and the solvent was evaporated. The crude material was purified by flash chromatography (silica gel, gradient of heptane in ethyl acetate) to provide the title compound as a light brown solid (5.47 g). MS (m/e): 356.1 ($MH^+$).

Step 4: (3α,6α)-8-[4-((R)-2,2,2-Trifluoro-1-methyl-ethoxy)-phenyl]-1-oxa-8-aza-dispiro[2.2.4.2]dodecan-7-one The title compound was prepared in analogy to example 3, step 6 by epoxidation of 2-[4-((R)-2,2,2-trifluoro-1-methyl-ethoxy)-phenyl]-2-aza-spiro[4.5]decane-1,8-dione. MS (m/e): 370.2 [$MH^+$].

Step 5: (5α,8α)-8-Hydroxy-8-((2-oxopyrrolidin-1-yl)methyl)-2-(4-((R)-1,1,1-trifluoropropan-2-yloxy)phenyl)-2-azaspiro[4.5]decan-1-one The title compound was prepared in analogy to example 1 step 7 from (3α,6α)-2-[4-((R)-2,2,2-trifluoro-1-methyl-ethoxy)-phenyl]-2-aza-spiro[4.5]decane-1,8-dione and 2-pyrrolidinone as a light yellow solid. MS (m/e): 445.214 [$MH^+$].

Example 10

(5α,8α)-8-Hydroxy-8-((2-oxopyrrolidin-1-yl)methyl)-2-(6-((S)-1,1,1-trifluoropropan-2-yloxy)pyridin-3-O-2-azaspiro[4.5]decan-1-one

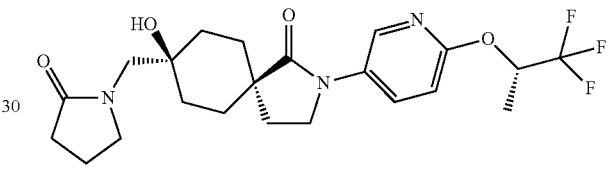

Step 1: 5-Nitro-2-((S)-2,2,2-trifluoro-1-methyl-ethoxy)-pyridine

In a 4-neck flask, commercially available 2-chloro-5-nitro-pyridine (71.9 g) and (S)-1,1,1-trifluoropropan-2-ol (54.3 g) were dissolved in DMF (610 ml) and sodium hydride (20 g, 55%) was added at a temperature of 16 to 18° C. (ice cooling). Following addition, the mixture was allowed to stir for 1 hour. The mixture was poured into ice and was allowed to hydrolyze. The suspension was warmed to RT over a period of 12 hours and the solid was filtered and washed with additional water and then with a small amount of hexanes (50 mL). The brown solid was further dried in vacuo to provide the title compound. (81.9 g). $^1$H-NMR (δ, $CDCl_3$): 9.06 (m, 1H), 8.43 (dd, 1H), 6.93 (d, 1H), 5.87 (m, 1H); 1.54 (m, 3H).

Step 2: 6-((S)-2,2,2-Trifluoro-1-methyl-ethoxy)-pyridin-3-ylamine

5-Nitro-2-((S)-2,2,2-trifluoro-1-methyl-ethoxy)-pyridine (81.9 g) and palladium on carbon (10% Pd, 0.0065 mol-eq) were added to MeOH and the mixture was hydrogenated until uptake of hydrogen was ceasing. The catalyst was removed by filtration and the filtrate was concentrated and further dried in vacuo to provide the title compound as a dark oil. MS (m/e): 207.0 ($MH^+$).

Step 3: 8-Hydroxy-2-[6-((S)-2,2,2-trifluoro-1-methyl-ethoxy)-pyridin-3-yl]-2-aza-spiro[4.5]decan-1-one The title compound was obtained in analogy to example 3 step 4 from 6-((S)-2,2,2-trifluoro-1-methyl-ethoxy)-pyridin- 3-ylamine (23.3 g) and 4-hydroxy-1-(2-methoxy-ethyl)-cyclohexanecarboxylic acid ethyl ester (20 g, obtained in example 3, step 3) as a brown oil (39.3 g). MS (m/e): 359.3 (MH+).

Step 4: 2-[6-((S)-2,2,2-Trifluoro-1-methyl-ethoxy)-pyridin-3-yl]-2-aza-spiro[4.5]decane-1,8-dione DMSO (16.3 ml) was added dropwise over a period of 5 minutes to a solution of 8-hydroxy-2-[6-((S)-2,2,2-trifluoro-1-methyl-ethoxy)-pyridin-3-yl]-2-aza-spiro[4.5]decan-1-one (39.3 g) in dichloromethane (400 ml) that was cooled down to −78° C. in a CO$_2$/acetone-bath. After 5 minutes, oxalylchloride (15.6 ml) was added dropwise over a period of 15 minutes and stirring was continued for 30 minutes at −78° C. Then, triethylamine (42.7 ml) was added dropwise over a period of 15 minutes to the reaction mixture and after 5 minutes, the mixture was allowed to warm to 20° C. and stirred further 2 h at R.T. The reaction mixture was poured into ice/water and was acidified with 2M aqueous HCl solution to pH 3. The aqueous phase was extracted two times with dichloromethane and the combined organic layers were washed with brine, dried over Na$_2$SO$_4$ and filtered. The solvent was evaporated and the residue was purified by flash chromatography (silica gel, gradient 20% to 60 of AcOEt in hexane) to give the title compound as an off white solid (23.96 g). MS (m/e): 357.2 (M(.

Step 5: (3α,6α)-8-[6-((S)-2,2,2-Trifluoro-1-methyl-ethoxy)-pyridin-3-yl]-1-oxa-8-aza-dispiro[2.2.4.2]dodecan-7-one The title compound was prepared in analogy to example 3, step 6 from 2-[6-((S)-2,2,2-trifluoro-1-methyl-ethoxy)-pyridin-3-yl]-2-aza-spiro[4.5]decane-1,8-dione as an off-white solid. MS (m/e): 371.3 [MH+].

Step 6: (5α,8α)-8-Hydroxy-8-((2-oxopyrrolidin-1-yl)methyl)-2-(6-((S)-1,1,1-trifluoropropan-2-yloxY)pyridin-3-yl)-2-azaspiro[4.5]decan-1-one The title compound was prepared in analogy to example 1, step 7 from (3α,6α)-8-[6-((S)-2,2,2-trifluoro-1-methyl-ethoxy)-pyridin-3-yl]-1-oxa-8-aza-dispiro[2.2.4.2]dodecan-7-one and 2-pyrrolidinone as an off white solid. MS (m/e): 445.210 [MH+].

Example 11

(5α,8α)-8-((2-Fluoroethoxy)methyl)-8-hydroxy-2-(6-((S)-1,1,1-trifluoropropan-2-yloxy)pyridin-3-yl)-2-azaspiro[4.5]decan-1-one

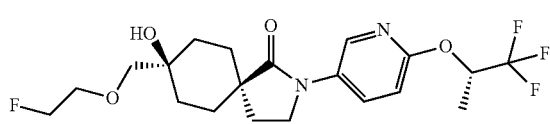 [SMILES: C[C@H](Oc1ccc(N2CC[C@]3(CC[C@@](O)(COCCF)CC3)C2=O)cn1)C(F)(F)F]

The title compound was prepared in analogy to example 8, step 5 from (3α,6α)-8-[6-((S)-2,2,2-trifluoro-1-methyl-ethoxy)-pyridin-3-yl]-1-oxa-8-aza-dispiro[2.2.4.2]dodecan-7-one and 2-fluorethanol as an off white solid. MS (m/e): 435.189 [MH+].

Example 12

(5α,8α)-8-((2-fluoroethoxy)methyl)-8-hydroxy-2-(4-isopropoxyphenyl)-2-azaspiro[4.5]decan-1-one

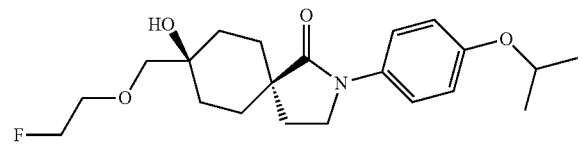 [SMILES: CC(C)Oc1ccc(N2CC[C@]3(CC[C@@](O)(COCCF)CC3)C2=O)cc1]

The title compound was prepared in analogy to example 8, step 5 from (3α,6α)-8-(4-isopropoxy-phenyl)-1-oxa-8-aza-dispiro[2.2.4.2]dodecan-7-one (prepared in example 3 step 6) and 2-fluorethanol as a brown solid. MS (m/e): 380.224 [MH+].

Example A

A compound of formula (I) can be used in a manner known per se as the active ingredient for the production of tablets of the following composition:

|  | Per tablet |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula (I) can be used in a manner known per se as the active ingredient for the production of capsules of the following composition:

|  | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

The invention claimed is:
1. A compound according to formula (I),

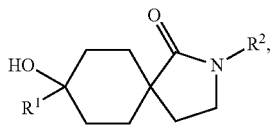

wherein
R¹ is selected from the group consisting of haloalkoxyalkyl, oxopyrrolydinylalkyl and oxopiperidinylalkyl; and
R² is substituted phenyl or substituted pyridinyl, wherein substituted phenyl and substituted pyridinyl are substituted with one to three substituents independently selected from the group consisting of haloalkyl, hydroxyhaloalkyl, alkoxy and haloalkoxy;
or a pharmaceutically acceptable salt or ester thereof.

2. A compound according to claim 1, wherein R¹ is haloalkoxyalkyl or oxopyrrolydinylalkyl.
3. A compound according to claim 1, wherein R¹ is haloalkoxyalkyl.
4. A compound according to claim 1, wherein R¹ is selected from the group consisting of 2-fluoroethoxymethyl, 2,2-difluoroethoxymethyl and 2,2,2-trifluoroethoxymethyl.
5. A compound according to claim 1, wherein R¹ is 2-fluoroethoxymethyl or 2,2-difluoroethoxymethyl.
6. A compound according to claim 1, wherein R¹ is 2-fluoroethoxymethyl.
7. A compound according to claim 1, wherein R¹ is 2,2-difluoroethoxymethyl.
8. A compound according to claim 1, wherein R¹ is 2,2,2-trifluoroethoxymethyl.
9. A compound according to claim 1, wherein R¹ is oxopyrrolydinylalkyl.
10. A compound according to claim 1, wherein R¹ is 2-oxopyrrolydin-1-ylmethyl.
11. A compound according to claim 1, wherein R¹ is oxopiperidinylalkyl.
12. A compound according to claim 1, wherein R¹ is 2-oxopiperidin-1-ylmethyl.
13. A compound according to claim 1, wherein R¹ is selected from the group consisting of 2-fluoroethoxymethyl, 2,2-difluoroethoxymethyl, 2,2,2-trifluoroethoxymethyl, 2-oxopyrrolydin-1-ylmethyl and 2-oxopiperidin-1-ylmethyl.
14. A compound according to claim 1, wherein R¹ is selected from the group consisting of 2-fluoroethoxymethyl, 2,2-difluoroethoxymethyl and 2-oxopyrrolydin-1-ylmethyl.
15. A compound according to claim 1, wherein R² is substituted phenyl or substituted pyridinyl, wherein substituted phenyl and substituted pyridinyl are substituted with one to three substituents independently selected from the group consisting of alkoxy and haloalkoxy.
16. A compound according to claim 1, wherein R² is substituted phenyl or substituted pyridinyl, wherein substituted phenyl and substituted pyridinyl are substituted with one substituent selected from the group consisting of trifluoromethyl, 2,2,2-trifluoro-1-hydroxyethyl, isopropoxy and 1,1,1-trifluoropropan-2-yloxy.
17. A compound according to claim 1, wherein R² is substituted phenyl, wherein substituted phenyl is substituted with one to three substituents independently selected from the group consisting of haloalkyl, hydroxyhaloalkyl, alkoxy and haloalkoxy.
18. A compound according to claim 1, wherein R² is substituted phenyl, wherein substituted phenyl is substituted with one substituent selected from the group consisting of haloalkyl, hydroxyhaloalkyl, alkoxy and haloalkoxy.
19. A compound according to claim 1, wherein R² is substituted phenyl, wherein substituted phenyl is substituted with one substituent selected from the group consisting of trifluoromethyl, 2,2,2-trifluoro-1-hydroxyethyl, isopropoxy and 1,1,1-trifluoropropan-2-yloxy.
20. A compound according to claim 1, wherein R² is substituted phenyl, wherein substituted phenyl is substituted with one substituent selected from the group consisting of isopropoxy and 1,1,1-trifluoropropan-2-yloxy.
21. A compound according to claim 1, wherein R² is 4-(isopropoxy)phenyl or 4-(1,1,1-trifluoropropan-2-yloxy)phenyl.
22. A compound according to claim 1, wherein R² is substituted phenyl, wherein substituted phenyl is substituted with one haloalkyl.
23. A compound according to claim 1, wherein R² is 4-(trifluoromethyl)phenyl.
24. A compound according to claim 1, wherein R² is substituted phenyl, wherein substituted phenyl is substituted with one hydroxyhaloalkyl.
25. A compound according to claim 1, 16 to 19 or 24, wherein R² is 4-(2,2,2-trifluoro-1-hydroxyethyl)phenyl.
26. A compound according to claim 1, wherein R² is substituted phenyl, wherein substituted phenyl is substituted with one alkoxy.
27. A compound according to claim 1, wherein R² is 4-(isopropoxy)phenyl.
28. A compound according to claim 1, wherein R² is substituted phenyl, wherein substituted phenyl is substituted with one haloalkoxy.
29. A compound according to claim 1, wherein R² is 4-(1,1,1-trifluoropropan-2-yloxy)phenyl.
30. A compound according to claim 1, wherein R² is substituted pyridinyl, wherein substituted pyridinyl is substituted with one to three substituents independently selected from the group consisting of haloalkyl, hydroxyhaloalkyl, alkoxy and haloalkoxy.
31. A compound according to claim 1, wherein R² is substituted pyridinyl, wherein substituted pyridinyl is substituted with one substituent selected from alkoxy and haloalkoxy.
32. A compound according to claim 1, wherein R² is substituted pyridinyl, wherein substituted pyridinyl is substituted with one substituent selected from isopropoxy and 1,1,1-trifluoropropan-2-yloxy.
33. A compound according to claim 1, wherein R² is 6-isopropoxypyridin-3-yl.
34. A compound according to claim 1, wherein R² is 6-(1,1,1-trifluoropropan-2-yloxy)pyridin-3-yl.
35. A compound according to claim 1 of formula (Ia)

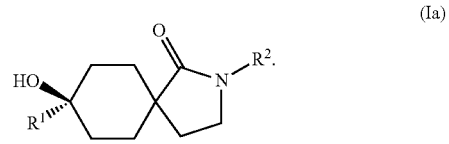

36. A compound according to claim 1 of formula (Ib)

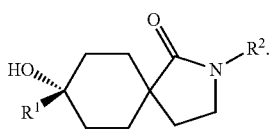

37. A compound according to claim 1, selected from the group consisting of:
- (5α,8α)-8-hydroxy-8-((2-oxopyrrolidin-1-yl)methyl)-2-(4-(trifluoromethyl)phenyl)-2-azaspiro[4.5]decan-1-one;
- (5α,8α)-8-Hydroxy-8-(2-oxo-piperidin-1-ylmethyl)-2-(4-trifluoromethyl-phenyl)-2-aza-spiro[4.5]decan-1-one;
- (5α,8α)-8-hydroxy-2-(4-isopropoxyphenyl)-8-((2-oxopyrrolidin-1-yl)methyl)-2-azaspiro[4.5]decan-1-one;
- (5α,8α)-8-hydroxy-2-(4-isopropoxyphenyl)-8-((2-oxopiperidin-1-yl)methyl)-2-azaspiro[4.5]decan-1-one;
- (5α,8α)-8-(2,2-Difluoro-ethoxymethyl)-8-hydroxy-2-(4-isopropoxy-phenyl)-2-aza-spiro[4.5]decan-1-one;
- (5α,8α)-8-Hydroxy-2-(6-isopropoxy-pyridin-3-yl)-8-(2-oxo-pyrrolidin-1-ylmethyl)-2-aza-spiro[4.5]decan-1-one;
- (5α,8α)-8-hydroxy-2-(6-isopropoxypyridin-3-yl)-8-((2,2,2-trifluoroethoxy)methyl)-2-azaspiro[4.5]decan-1-one;
- (5α,8α)-8-Hydroxy-8-(2-oxo-pyrrolidin-1-ylmethyl)-2-[4-((R)-2,2,2-trifluoro-1-hydroxy-ethyl)-phenyl]-2-aza-spiro[4.5]decan-1-one;
- (5α,8α)-8-hydroxy-8-((2-oxopyrrolidin-1-yl)methyl)-2-(4-((R)-1,1,1-trifluoropropan-2-yloxy)phenyl)-2-azaspiro[4.5]decan-1-one;
- (5α,8α)-8-hydroxy-8-((2-oxopyrrolidin-1-yl)methyl)-2-(6-((S)-1,1,1-trifluoropropan-2-yloxy)pyridin-3-yl)-2-azaspiro[4.5]decan-1-one;
- (5α,8α)-8-((2-fluoroethoxy)methyl)-8-hydroxy-2-(6-((S)-1,1,1-trifluoropropan-2-yloxy)pyridin-3-yl)-2-azaspiro[4.5]decan-1-one;
- (5α,8α)-8-((2-fluoroethoxy)methyl)-8-hydroxy-2-(4-isopropoxyphenyl)-2-azaspiro[4.5]decan-1-one;

and pharmaceutically acceptable salts thereof.

38. A compound according to claim 1, selected from the group consisting of:
- (5α,8α)-8-hydroxy-2-(4-isopropoxyphenyl)-8-((2-oxopyrrolidin-1-yl)methyl)-2-azaspiro[4.5]decan-1-one;
- (5α,8α)-8-(2,2-Difluoro-ethoxymethyl)-8-hydroxy-2-(4-isopropoxy-phenyl)-2-aza-spiro[4.5]decan-1-one;
- (5α,8α)-8-((2-fluoroethoxy)methyl)-8-hydroxy-2-(6-((S)-1,1,1-trifluoropropan-2-yloxy)pyridin-3-yl)-2-azaspiro[4.5]decan-1-one;

and pharmaceutically acceptable salts thereof.

39. A pharmaceutical composition comprising a compound according to claim 1 and a therapeutically inert carrier.

* * * * *